United States Patent [19]

Vanderwater

[11] Patent Number: 4,884,887

[45] Date of Patent: Dec. 5, 1989

[54] METHOD FOR POSITIONING A CRYSTAL INGOT

[75] Inventor: David A. Vanderwater, Santa Clara, Calif.

[73] Assignee: Hewlett-Packard Company, Palo Alto, Calif.

[21] Appl. No.: 6,396

[22] Filed: Jan. 23, 1987

[51] Int. Cl.⁴ ............................................. G01N 21/00
[52] U.S. Cl. ...................................................... 356/31
[58] Field of Search ............................ 356/30, 31, 445

[56] References Cited

U.S. PATENT DOCUMENTS 2,423,357  7/1947  Watrodski ............................... 356/31
2,858,730 11/1958  Hanson ................................... 356/31
3,782,836  1/1974  Fey et al. ............................... 356/30

Primary Examiner—Richard A. Rosenberger

[57] ABSTRACT

An apparatus is disclosed for use with a device for processing a crystal having crystallographic axes and crystallographic facets on its surface. A light beam is supplied towards the facets where the light beam has a selected spatial relationship to the device. The directions of reflections of the light beam from the facets are detected to determine the spatial relationship between one crystallographic axis and the processing device so that the body is processable using the device in reference to the crystallographic axis. A U-shaped member is placed with its open ends in contact with or adjacent to a reference surface of the processing device. The U-shaped member encloses and is urged against the body when the body is rotated about a reference direction of the device The U-shaped member is of such dimensions that the surface portions of the body at distances smaller than a predetermined distance will cause both ends of the member to contact the reference surface.

11 Claims, 2 Drawing Sheets

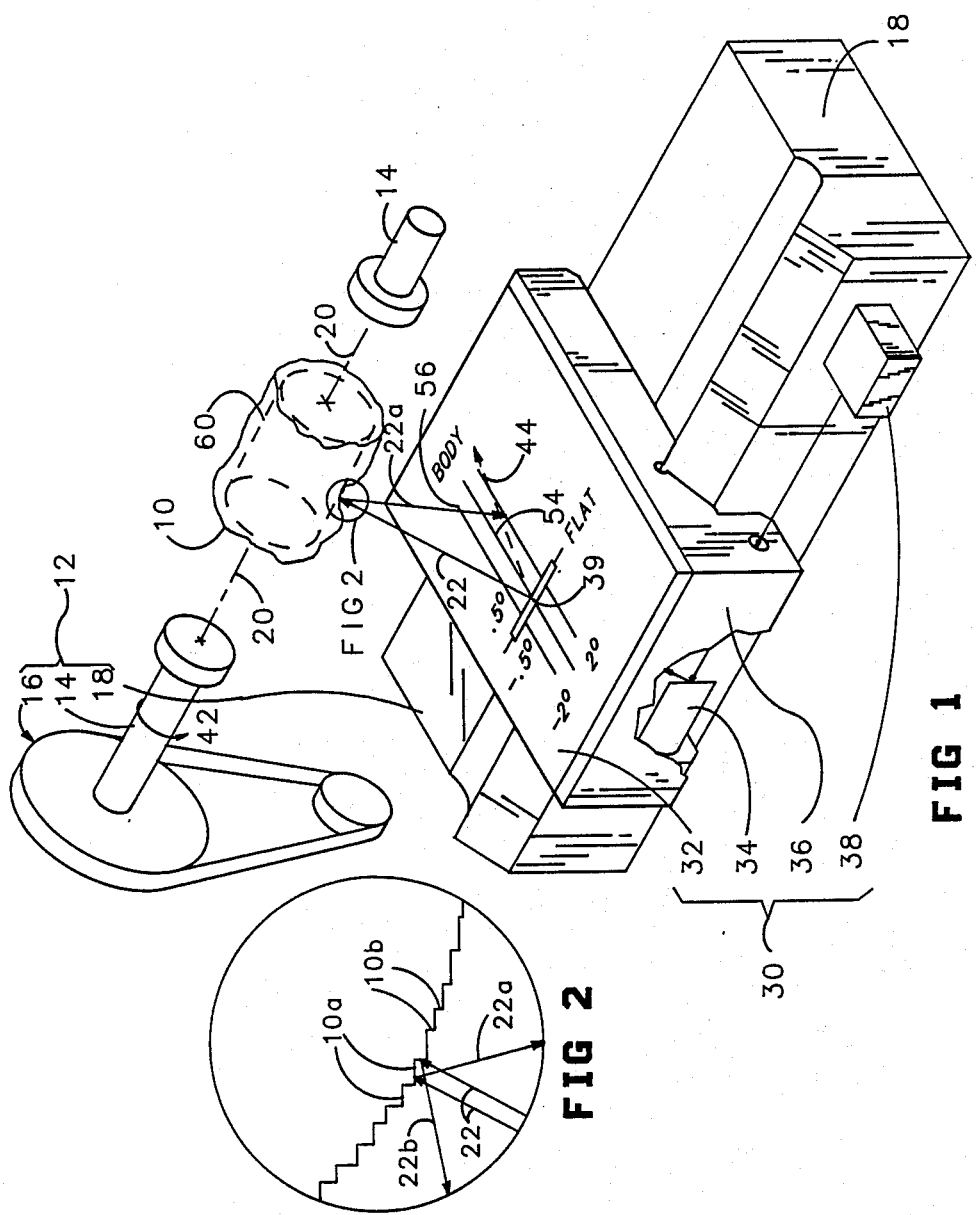

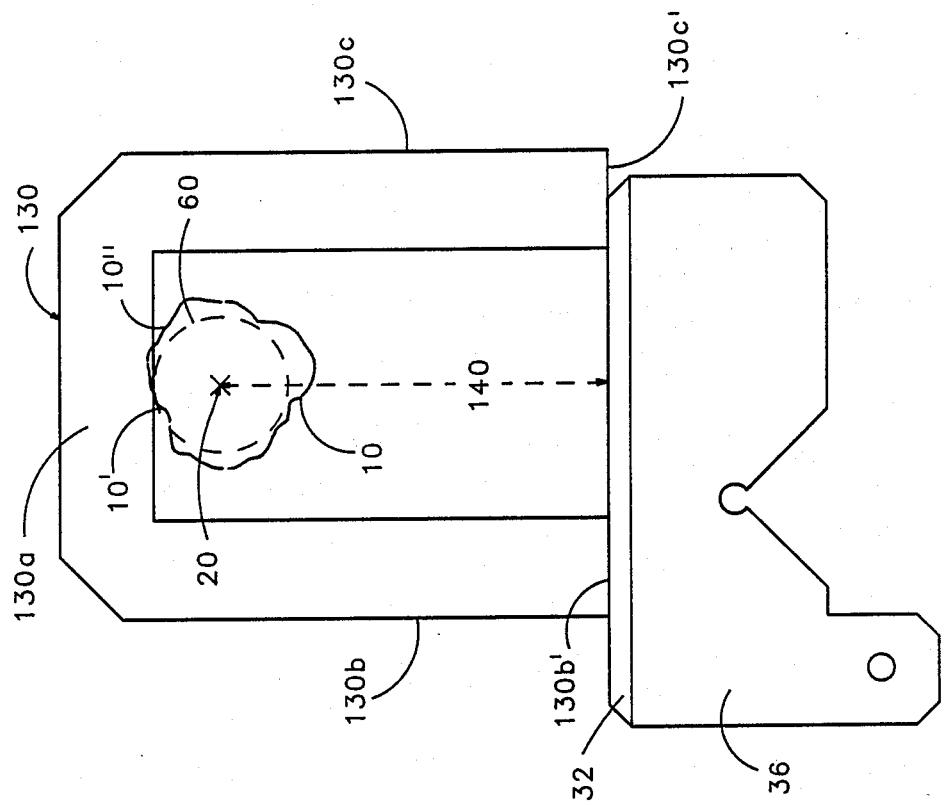

METHOD FOR POSITIONING A CRYSTAL INGOT

BACKGROUND OF THE INVENTION

This invention relates to a system for detecting the spatial relationship between a crystalline body and the processing reference direction of a processing device so that the crystalline body may be positioned at a desired location and orientation relative to the machine to facilitate processing.

In the manufacture of semiconductor wafers, the wafers are cut from single crystal ingots. Typically these ingots are irregular in shape. To facilitate subsequent processing, the ingot is normally shaped by removing material from its surface to leave an accurately shaped ingot, such as a cylinder.

The ingot shaping step is typically performed on commercially available machines such as the grinding machine manufactured by Ueda Giken Co. of Japan and available in the United States through Cybeq Systems of Menlo Park, Calif. The Ueda grinding machine has a reference processing direction. The machine has means for holding the ingot with the ingot intersected by the processing reference direction and means for rotating the ingot about the processing reference direction. A tangentially oriented cup-shaped grinding wheel passes along the processing direction removing material from the surface of the ingot while the ingot is rotated. Ingots in the shape of accurate cylinders are obtained.

The cylindrical ingot obtained is then sliced into wafers with specific crystallographic orientations. Typically, it is desirable for the wafers to have <100> or <111> orientations, that is, the planar surfaces of the wafers are substantially normal to their crystallographic <100> or <111> directions. For this reason, it is necessary that the ingot is shaped so that the axis of the cylinder is along one of the <100> or <111> directions.

It is known that, under proper conditions, an ingot may be sandblasted or chemically etched, leaving an ingot surface composed of microscopic crystallographic facets. For Gallium Arsenide ingots, for example, microscopic facets will form on the {110} planes. Light reflected by these microscopic facets will be specularly reflected.

Similar preferential cleavage properties have been used by Hewlett Packard Company to determine the crystallographic orientation of a wafer sliced from an ingot. A single wafer is sliced from the ingot, the wafer cleaved exposing {110} planes, the wafer edge illuminated by a LASER beam, and the reflections of the LASER from the wafer edge observed to determine the crystallographic orientation of the wafer surface. Adjustments are then made to the saw in subsequent slicing operations. To allow an operator to translate the mis-orientation angles into saw adjustments, it is necessary to develop techniques and translation graphs to aid the translation of the mis-orientation angles into saw adjustments.

Other conventional optical devices have been used to determine the orientation of a crystal. One such optical device is the Model 210 Optical Orientation Instrument available from South Bay Technology, Inc. of Temple City, Calif. Model 210 uses a LASER beam to determine the orientation of a crystal. The LASER beam is reflected off a cleaved or preferentially etched crystal surface back onto a target that is perpendicular to the incident LASER beam.

After the orientation of an ingot is determined using model 210, it is necessary to record the crystallographic orientation of the ingot in reference to a known reference frame and then use the information recorded to position the ingot with its selected crystallographic axis substantially coinciding with the processing direction of the grinding machine. In conventional systems, this requires sophisticated and expensive instruments such as goniometers and highly skilled personnel to operate the instruments.

None of the above described conventional systems for placing a crystalline ingot in the desired position for processing are entirely satisfactory. It is therefore desirable to provide improved systems whereby the above-described difficulties are alleviated.

SUMMARY OF THE INVENTION

This invention is based on the recognition that the placing of the ingot with its crystallographic orientation properly aligned with the processing direction of a processing machine can be much simplified by detecting the crystallographic orientation of the ingot relative to the processing direction. By using the processing machine as the reference frame, the subsequent step of aligning a selected crystallographic axis with the processing reference direction becomes simple.

The apparatus of this invention is suitable for use with a device for processing a crystalline body having crystallographic axes and crystallographic facets on its surface, where the device includes means for processing the body in reference to a processing reference direction. The apparatus is suitable for detecting the spatial relationship between the processing reference direction and one of the crystallographic axes. The apparatus comprises means for supplying a light beam towards facets on the surface of the body, said light beam being in a direction with a selected spatial relationship to the processing reference direction. The apparatus further comprises means for detecting the directions of reflections of the light beam from the facets to determine the spatial relationship between said one crystallographic axis and the processing reference direction, so that the body is processable using the device in reference to said one crystallographic axis.

Another aspect of the invention is directed towards an apparatus suitable for use with a device for processing a body in reference to processing reference direction, said device including a reference surface at a selected distance from the processing direction and means for holding the body so that the processing direction intersects the body and for rotating the body about the processing reference direction. The apparatus is suitable for detecting whether the surfaces of portions of the body are farther than a predetermined distance from the reference surface when the body is held and rotated about the processing reference direction. The apparatus comprises a U-shaped member having two ends. When the ends of the U-shaped member are placed in contact with or adjacent to the reference surface with the U-shaped member enclosing and urged against the crystalline body, and when the body is held and rotated about the processing reference direction, surface portions of the body at distances smaller than the predetermined distance will cause the two open ends of the U-shaped member to both contact the reference surface.

BRIEF DESCRIPTION OF THE DRAWINGS

FIG. 1 is an isometric view of a portion of a processing device, a crystalline ingot and an apparatus for detecting the crystallographic orientation of the ingot relative to a processing direction of the processing device to illustrate the preferred embodiment of the invention.

FIG. 2 is an exploded cross-sectional view of a portion of the ingot shown in circle 2 in FIG. 1, the cross section being taken in the plane containing a light beam and its reflection from the facets on the surface of the ingot to illustrate the preferred embodiment of the invention.

FIG. 3 is an elevational view of a portion of a processing device and of an apparatus for detecting whether the distances between portions of the surface of an ingot to a processing reference direction of the processing device are greater than a predetermined distance to illustrate the preferred embodiment of the invention.

DETAILED DESCRIPTION OF THE INVENTION

FIG. 1 is an isometric view of a portion of a processing device and an apparatus for detecting the crystallographic orientation of an ingot relative to a processing reference direction of the device to illustrate the preferred embodiment of the invention. As shown in FIG. 1, a crystalline ingot 10 is held by the holding means of a processing device 12 which includes a holding means 14, rotating means 16 and a way and gib 18. The processing device is designed to process (e.g. grind) ingot 10 in reference to a processing reference direction 20. Frequently the holding means 14 comprises a pair of clamping rams as shown in FIG. 1. The apparatus 30 for detecting the crystallographic orientation of ingot 10 relative to direction 20 supplies a light beam 22 in a direction with a selected spatial relationship to the processing reference direction 20. Light beam 22 impinges on the surface of ingot 10 and is reflected in different directions.

Ingot 10 has crystallographic axes and crystallographic facets on its surface. The facets can be created either by sand blasting or by chemical etching. The microscopic facets on the surface of ingot 10 will reflect beam 22 in different directions, forming a pattern analogous with a Laue X-ray pattern. By detecting the directions of reflections of beam 22, the crystallographic orientation of ingot 10 can be determined in reference to the light beam 22. Since beam 22 has a known spatial relationship to the processing reference direction 20, the crystallographic orientation of ingot 10 with respect to the processing direction 20 can be determined in a simple manner. The crystallographic orientation of ingot 10 with respect to the direction of light beam 22 can be determined in the conventional manner from the directions of reflections of beam 22. In the preferred embodiment, the apparatus 30 for detecting the crystallographic orientation of ingot 10 comprises a screen 32 adjacent to ingot 10. As shown in FIG. 1 at least some of the reflections by the microscopic facets of ingot 10 of beam 22 are intercepted by screen 32. By observing the pattern of the reflections on screen 32, the crystallographic orientation of ingot 10 relative to beam 22 can be determined.

Thus, the system of this invention utilizes the processing reference direction 20 of the processing device 12 as its reference. Consequently the crystallographic orientation of ingot 10 relative to direction 20 can be determined in a manner much simpler than that required by prior art devices. If the direction of beam 22 is chosen to have a simple spatial relationship to direction 20 as in the preferred embodiment, the process of determining the crystallographic orientation of ingot 10 relative to direction 20 can be further simplified as described below. However, before describing in further detail the preferred embodiment, it is necessary to describe in some detail the microscopic facets on the surface of ingot 10 and how they reflect beam 22.

FIG. 2 is a cross-sectional view of a portion of ingot 10 taken along a plane that contains beam 22 and some of the reflections of beam 22, the view in FIG. 2 being an exploded view of the portion of ingot 10 within circle 2 in FIG. 1. The crystallographic structure of ingot 10 is assumed to be cubic, it will be understood that if ingot 10 has a crystal structure other than cubic, the invention will function in essentially the same manner as described herein. Thus, the invention is equally applicable where the crystal structure of ingot 10 is not cubic.

As shown in FIG. 1, while ingot 10 has an irregular surface, it is roughly cylindrical in shape. When ingot 10 is sandblasted or chemically etched, the "cylindrical" surface of the ingot will consists of particular crystallographic planes. For certain crystals, one particular family of crystallographic planes may predominate. For Gallium Arsenide, for example, {110} planes will be dominant. If ingot 10 is a Gallium Arsenide crystal and if a cross-section of ingot 10 is taken along a {100} plane, the microscopic facets on its "cylindrical" surface will resemble a staircase formed by two types of microscopic facets labeled 10a, 10b. As can be seen in FIG. 2, the two types of facets are normal to each other. When a light beam, such as beam 22, impinges on the surface of ingot 10, facets 10a and 10b reflect the beam along directions 22a, 22b respectively. As shown in FIG. 2, beam 22 is in such direction relative to facets 10a, 10b that beam 22 is about 5 to 10 degrees from a direction normal to facets 10a. Hence, the reflection 22a bears a small angle to beam 22. Beam 22, however, are at a much greater angle to the normal of facets 10b so that reflections 22b are at large angles to beam 22 as shown in FIG. 2. In FIG. 2, beam 22 is shown with a very small width so that it impinges on only one of the 10a facets and only one of the 10b facets. Where beam 22 is wider, as is usually the case, beam 22 would impinge on many or all of the facets in FIG. 2. As will be apparent from FIG. 2, a greater portion of beam 22 will be reflected by facets 10a than 10b so that reflection 22a is much stronger in intensity than 22b. Where beam 22 is in a direction at approximately equal angles to facets 10a, 10b, the two reflections will be of substantially the same intensity.

Instead of having to decipher a complex reflection pattern as described above, the determination of the orientation of ingot 10 can be simplified if the direction of beam 22 is chosen so that strong reflections, such as reflection 22a, are observed. As an initial step to simplify the procedure, the direction of beam 22 is chosen so that it is incident upon ingot 10 along a direction substantially orthogonal to direction 20. As described above, depending on the orientation of beam 22 relative to the facets, a predominant direction of reflection can be detected for certain orientations of beam 22. For this purpose the rotation means 16 of device 12 may be utilized in order to simplify the procedure. Thus, in the preferred embodiment, ingot 10 is rotated about the processing reference direction 20 by rotation means 16. As ingot 10 is rotated along the arrow 42 shown in FIG. 1, the normals to facets 10a will be at greater angles to beam 22 causing the reflections 22a to be at greater angles to beam 22. The reflection 22a intercepted by screen 32 will therefore travel along a direction 44 shown in FIG. 1.

If a <100> direction of ingot 10 coincides with or is close to processing reference direction 20, line 44 will lie in the plane substantially normal to direction 20 and containing beam 22. In this case, the process of detecting the crystallographic orientation of ingot 10 and the adjusting its orientation to align its <100> axis with direction 20 is greatly simplified. Line 54 represents the intersection of screen 32 with a plane normal to direction 20 and containing beam 22. Therefore, if a <100> axis of ingot 10 is exactly aligned with direction 20, the path 44 traversed by reflection 22a will coincide with line 54. Where a <100> axis of ingot 10 is at a small angle to direction 20, path 44 will be displaced from or at a small angle to line 54 as is the case shown in FIG. 1. Upon observing that path 44 deviates from line 54, the orientation of ingot 10 can be adjusted slightly until, upon the next rotation, path 44 coincides substantially with line 54. Where some slight inaccuracies in alignment can be tolerated, lines 56 close to line 54 are drawn to mark the tolerance limit. All an operator would have to do is to observe whether path 44 falls within the tolerance limits and adjust the orientation of ingot 10 until it does. No expensive equipment such as a goniometer is required and persons with low skill levels can operate the system efficiently and accurately. Once ingot 10 has been adjusted so that a selected crystallographic axis is aligned with direction 20, device 12 is then operated to process ingot 10 into a desired shape such as a cylindrical shape shown in dotted lines 60 in FIG. 1.

In semiconductor wafer manufacturing, it is customary to grind a crystallographic oriented flat on one side of the wafer. For this reason, it is frequently desirable to grind a flat on one side of cylinder 60 so that when the cylinder is sliced, wafers with flats will result. Apparatus 30 of FIG. 1 can again be used for determining the orientation of the crystallographic planes so that the flat ground on cylinder 60 using device 12 is accurately aligned along such planes.

By shining a light beam on the surface of cylinder 60 and detecting the directions of the reflections from the microscopic facets in the form of a pattern of reflections on screen 32, the orientation of the {110} planes can be ascertained. Then from the distance between the cylinder and the light source and the pattern of reflections, the position for grinding the flat can be determined. A simplified method for determining the orientation of the {110} planes is based on the observation that if cylinder 60 is rotated until reflections 22a coincides with beam 22, beam 22 is normal to some of the facets such as facets 10a, and the direction of beam 22 will coincide with the direction of a {110} plane. Hence, when cylinder 60 is rotated about direction 20 until reflection 22a coincides with beam 22, cylinder 60 can simply be ground along a plane with beam 22 as its normal. This method is advantageous since the determination can be performed easily and accurately by unskilled personnel without requiring the knowledge of the distance between the surface of cylinder 60 and the screen.

Apparatus 30 comprises a screen 32, a mirror 34, a support 36 and a light source 38. Light source 38 supplies a light beam substantially parallel to direction 20. The light beam supplied by source 38 is reflected by mirror 34 through a hole 39 in screen 32 towards ingot 10. Support 36 is shaped to ride on way and gib 18 so that it can be moved along the way and gib while maintaining beam 22 in a direction substantially normal to processing reference direction 20. Since some portions of the surface of ingot 10 reflect light better than other portions, it is advantageous for light beam 22 to be movable along a direction parallel to direction 20 while maintaining beam 22 orthogonal to direction 20, so that an operator can select portions of the surface of ingot 10 which are better light reflectors. By providing a light source 38 which supplies light in a direction parallel to direction 20 and support 36 which can be moved along a direction also parallel to direction 20, the direction of beam 22 is maintained substantially orthogonal to direction 20 while support 36 and mirror 34 are moved. In the preferred embodiment the light being supplied by source 38 is a LASER beam.

Where cylinder 60 resulting from the grinding of ingot 10 is an accurate cylinder, the wafers subsequently sliced from cylinder 60 will have circular shapes. If ingot 10 happens to have a "hole" in its cylindrical surface so that the resulting cylinder 60 also has a hole in its cylindrical surface, one or more wafers sliced from cylinder 60 will have an irregular shape. This is undesirable. It is also preferable to detect the "holes" before the grinding operation so that the ingot can be simply repositioned to allow a complete cylinder to be ground. For this purpose a U-shaped centering gauge 130 may be used as shown in FIG. 3. Gauge 130 has a base portion 130a, and two side portions 130b, 130c. Each of the two side portions has one end connected to the base portion and an open end 130b' and 130c' as shown in FIGS. 1 and 4, the processing reference direction 20 is at a selected distance 140. The shape of member 130 is such that when ends 130b' and 130c' are in contact with the top surface of screen 32 when screen 32 and support 36 are placed on top of way and gib 18, with member 130 enclosing direction 20, the distance between base portion 130a to screen 32 is substantially equal to the sum of the selected distance d and the desired radius of cylinder 60. After a selected crystallographic axis of ingot 10 has been aligned with processing reference direction 20, member 130 can be used to determine whether ingot 10 is large enough so that after grinding, a cylinder 60 with a perfect cylindrical surface will result. As shown in FIG. 3, ingot 10 has a portion 10' whose distance to direction 20 is smaller than the radius of the desired cylinder 60. Hence, when ingot 10 is ground, an imperfect cylinder will result which has a depression with surface 10'. This can be detected before the grinding operation by placing member 130 with base portion 130a in contact with ingot 10 in a manner shown in FIG. 3. When portion 130a is urged against (e.g. by gravity) a surface portion of ingot 10 whose distance to direction 20 is greater than the radius of a desired cylinder 60, such as surface portion 10", at least one of the two ends 130b' and 130c' will be lifted off the screen 32. Thus, if one of the two ends is lifted above screen 32 at all times when ingot 10 is rotated about direction 20, then all surface portions of ingot 10 in contact with member 130 are at distances to direction 20 which are greater than the desired radius of cylinder 60. If, however, both ends are in contact with screen 30 at any one instant, it indicates that the surface portion of ingot 10 in contact with member 130 at such instant will be at a distance less than the radius of cylinder 60. The operator's attention is then drawn to such surface portion of ingot 10 for further determination to see if the ingot should be repositioned or discarded. This process can be repeated for different parts of ingot 10 to ensure that all "cylindrical" surface portions of ingot 10 are at distances to direction 20 greater than the radius of cylinder 60.

The above description of the construction of the apparatus and the steps of the method are merely illustrative thereof and various changes in the details may be within the scope of the appended claims.

I claim:

1. A method for positioning an ingot of crystalline material with respect to a device for processing the ingot in reference to a preselected processing reference direction of the device so that a crystallographic axis of the ingot has a desired spatial relationship to the preselected processing reference direction, comprising the steps of:
   directing an incident light beam onto a spot on the ingot and causing reflection of a light beam;
   detecting the reflected beam on a surface;
   rotating the ingot about an axis of rotation;
   detecting a line of travel of the reflected beam onto the surface as the ingot is rotated;
   comparing the line of travel to a limit line on the surface, the limit line having a known relationship to the processing reference direction; and
   re-positioning the ingot such that the crystallographic axis has the desired relationship to the processing reference direction in order to allow processing of the ingot along the processing reference direction by means of the device without requiring any further positioning step.

2. A method as in claim 1, further comprising an initial step of positioning the ingot, surface and light beam such that the strong beam is strong relative to other beams reflected from the spot.

3. A method as in claim 2, wherein the initial step further comprises positioning the ingot such that the ingot longitudinal axis is the axis of rotation and such that the axis of rotation is initially aligned parallel to the processing reference direction.

4. A method as in claim 3, wherein the step of direction the light beam comprises directing the light beam onto the spot along an incident path substantially orthogonal to the processing reference direction.

5. A method as in claim 4, wherein the step of repositioning comprises re-positioning the ingot so that the line of travel is parallel to the limit line.

6. A method as in claim 4, wherein the step of repositioning comprises re-positioning the ingot so that the line of travel is close to the limit line.

7. A method as in claim 4, wherein the step of repositioning comprises re-positioning the ingot so that the line of travel lies between the limit line and a second limit line spaced apart by a distance representing allowable ingot positioning tolerance.

8. A method as in claim 4, wherein the initial step of positioning comprises positioning the surface so that the strong beam is orthogonal to the surface.

9. A method as in claim 4, further comprising, before the step of directing, a step of preparing a crystallographic oriented flat at the spot to expose crystallographic facets.

10. A method as in claim 4, wherein the step of rotating comprises rotating the ingot until the strong beam lies along the path of the incident beam.

11. An apparatus for positioning an ingot of crystalline material with respect to a device for processing the ingot in reference to a preselected processing reference direction of the device so that a crystallographic axis of the ingot has a desired spatial relationship to the preselected processing reference direction, comprising the steps of:
   means for directing an incident light beam onto a spot on the ingot and causing reflection of a light beam;
   means for detecting the reflected beam on a surface;
   means for rotating the ingot about an axis of rotation;
   means for detecting a line of travel of the reflected beam onto the surface as the ingot is rotated;
   means for comparing the line of travel to a limit line on the surface, the limit line having a known relationship to the processing reference direction; and
   means for re-positioning the ingot such that the crystallographic axis has the desired relationship to the processing reference direction in order to allow processing of the ingot along the processing reference direction by means of the device without requiring any further positioning step.

* * * * *